United States Patent [19]

Kohayakawa

[11] 4,257,687
[45] Mar. 24, 1981

[54] EYE EXAMINING INSTRUMENT WITH PHOTO-DETECTING SYSTEM

[75] Inventor: Yoshimi Kohayakawa, Yokohama, Japan

[73] Assignee: Canon Kabushiki Kaisha, Tokyo, Japan

[21] Appl. No.: 893,525

[22] Filed: Apr. 4, 1978

[30] Foreign Application Priority Data

Apr. 12, 1977 [JP] Japan .................................. 52/41721

[51] Int. Cl.³ .......................... A61B 3/14; G03B 29/00
[52] U.S. Cl. .......................................... 351/7; 354/62; 351/14
[58] Field of Search ............... 356/153, 399, 4; 351/1, 351/6, 13, 16, 9, 7, 14; 350/2; 354/62

[56] References Cited

U.S. PATENT DOCUMENTS

| | | | |
|---|---|---|---|
| 3,724,932 | 4/1973 | Cornsweet et al. | 351/7 |
| 3,813,166 | 5/1974 | Mary | 356/4 X |
| 3,864,030 | 2/1975 | Cornsweet | 356/4 |
| 3,915,564 | 10/1975 | Urban | 351/7 |
| 4,040,740 | 8/1977 | Handtmann et al. | 356/4 |

OTHER PUBLICATIONS

Crane et al., Accurate Three-Dimensional Eyetracker, App. Optics, v. 17n5, 3/78, pp. 691–705.

*Primary Examiner*—John K. Corbin
*Assistant Examiner*—Rodney B. Bovernick
*Attorney, Agent, or Firm*—Toren, McGeady and Stanger

[57] ABSTRACT

An ophthalmoscopic instrument having an infrared image converter tube for observation and/or examination of an ocular fundus prior to recording an image thereof provided with a range finding device which assists in establishing a suitable working distance between an eye and an objective lens in the instrument optically aligned to each other. A light beam is projected onto the iris of an eye to be examined or the cornea thereof near or at the center and is transmitted by scattering reflection or regular reflection respectively from the iris or cornea to a photo-detecting system which produces an electrical output signal capable of reaching a peak value only when the transmitted light enters a slit ahead of a light sensitive surface or strikes that one of light sensitive segments which is adapted to be the most light responsive, as the device is moved in unison with the instrument body.

8 Claims, 6 Drawing Figures

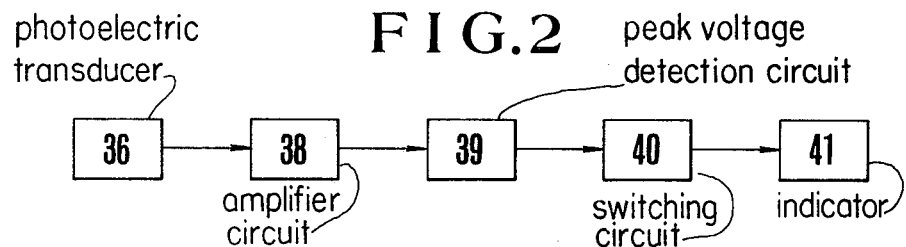
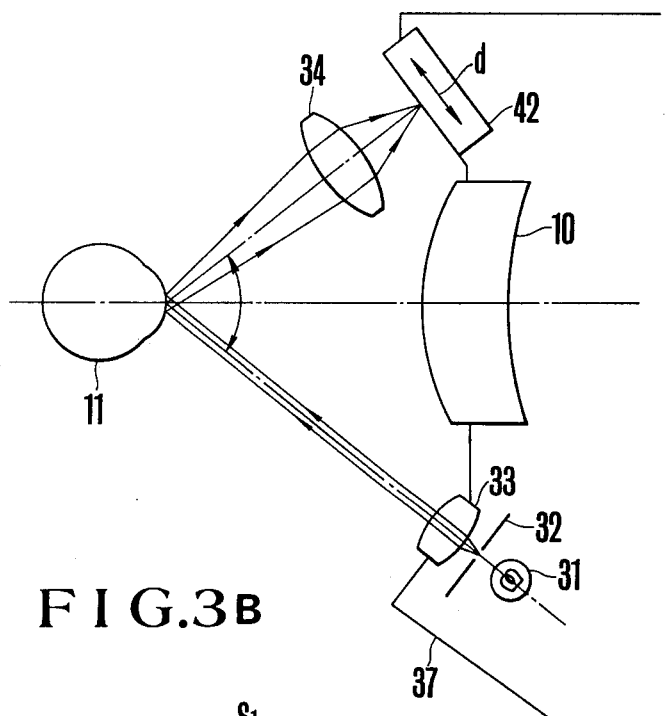
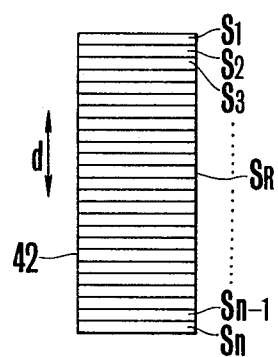

EYE EXAMINING INSTRUMENT WITH PHOTO-DETECTING SYSTEM

BACKGROUND OF THE INVENTION

This invention relates to ophthalmoscopic instruments and, more particularly, to a range finding device adapted for use with such ophthalmoscopic instrument.

The preliminary adjustment of an ophthalmoscopic instrument in its position with respect to an eye to be examined in an important operation. In the case of an ophthalmoscopic camera, for example, while looking for a target area near or at the pupil of the eye, the operator will first perform aligning of the optical axis of the camera to that of the eye with the help of an illuminated area on the cornea of the eye by an illuminating light beam projected from an objective lens of the camera. Then, he will turn to look through a finder of the camera for the purpose of obtaining a sharp image of the fundus of the eye, namely the retina, by moving the camera, so as to provide a suitable working distance between the camera and the eye to be examined. The term "working distance" herein used, though being generally accepted to mean the object distance for the objective lens system, is intended to refer to what is known in ophthalmoscopic art as an axial separation between the objective lens and the eye to be examined.

It is known to provide an ophthalmoscopic instrument of the type in which infrared light is made use of in illuminating an eye to be examined. With this type ophthalmoscopic camera, it is of course very difficult to achieve visual adjustment of the position and alignment of the camera relative to the eye since infrared light can hardly be viewed by the human eye. Even when the infrared image is converted to a corresponding visible image, it is difficult to achieve accurate adjustment of the working distance and also to prevent introduction of uncertainties in the later focusing procedure, since the resolving power of the infrared image converter tube is not so high as desired.

Attempts have been made to realize the condition of appropriate aligning and spacing of an ophthalmoscopic instrument of the type described to and from an eye to be examined by making use of a sight on one side of the instrument housing to correct for range in such a manner that while the cornea of the eye is illuminated by infrared light uniformly, the instrument housing is moved to bring the center of the field of view of the sight into coincidence with the pupil of the eye, for example, disclosed in U.S. Pat. No. 3,871,772. In another instrument, the sight may be otherwise used to view an image of a chart formed on the cornea. In any case, however, the visual adjusting procedure suffer from various uncertainties due to the difference among individuals in the spectral response of their eyes and it is difficult to perform because the operator is required to look through the eye-piece of the sight during that procedure.

SUMMARY OF THE INVENTION

An object of the present invention is to provide an ophthalmoscopic instrument having a range finding device for assisting an operator in judging the point for providing a suitable working distance between the instrument and an eye to be examined.

Another object of the invention is to provide a range finding device which enables accurate axial alignment of the instrument with the eye to be examined.

The present invention contemplates the use of a photo-electric transducer in constructing such range finding device. Many examples of arrangement of this photo-electric transducer are possible: One is that an optical path through which a light beam projected onto a front part of an eye to be examined is transmitted by scattering or regular reflection to the photo-electric transducer is arranged in fixed relation to an optical path through which the light beam is projected, so that the output of the transducer reaches a peak value when the condition of appropriate aligning and spacing of the instrument is realized, and the second is that, while the latter optical path is maintained in fixed relation to the optical axis of the objective lens of the instrument, the position of the transmission light path is varied as the spatial relation between the objective lens and the eye is varied, so that the transducer produces a dip or peak output when the actual transmission light path coincides with a reference one.

For the light beam, use may be made of a visible light of high intensity when a mydriatic is given to a person whose eyes are to be examined. Without the use of the mydriatic, it is required that the intensity and spectral region of the light beam be changed so as not to cause reduction of the size of the pupil of the eye.

BRIEF DESCRIPTION OF THE DRAWINGS

FIG. 2 is a block diagram of exemplary circuitry employed for processing the output of a photo-cell of FIG. 1.

FIG. 3A is a schematic view of another embodiment of the invention.

FIG. 3B is a plan view of a position detector of FIG. 3A.

DESCRIPTION OF THE PREFERRED EMBODIMENTS

Figure 1:
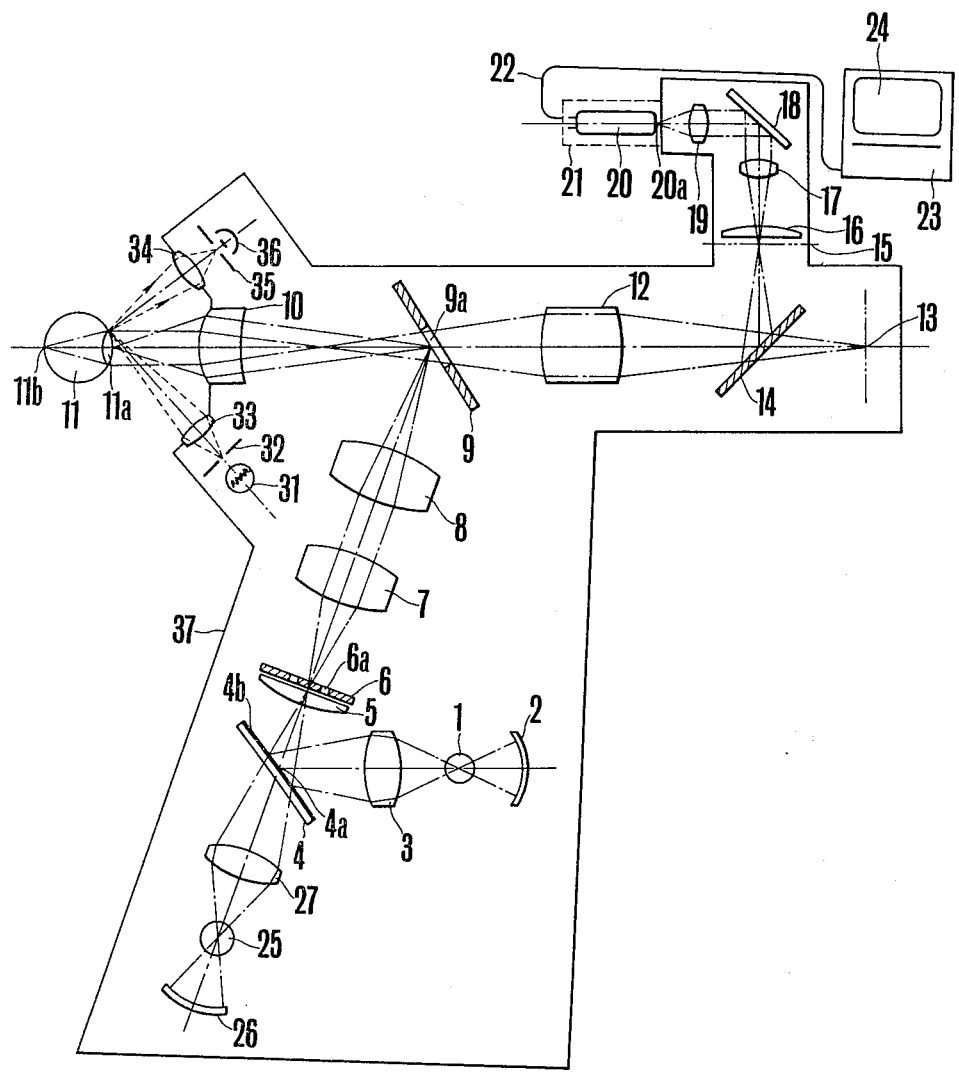
FIG. 1 is a schematic view of one embodiment of a range finding device according to the present invention applied to an ophthalmoscopic camera.

Referring to FIG. 1, there is shown one embodiment of a range finding device according to the invention incorporated within a common housing 37 of an ophthalmoscopic camera. The housing 37 further accommodates an illuminating optical system having selective control of spectral region of light for examination and photography of the fundus 11b of an eye 11. The illuminating optical system includes a first light source 1 in the form of an incandescent lamp, a reflector 2 positioned behind the lamp 1, a condenser lens 3 which forms an intermediate image of the light source 1 nearly in coincidence with a diaphragm 6 having a ring-shaped aperture 6a formed therein after reflection from an inclined mirror 4 and then passing through a field lens 5, and a relay lens of two components 7 and 8 which forms a further intermediate image of the light source 1 upon an illuminating mirror 9 placed at an acute angle to the optical axis of a photographic objective lens 10. The first-named mirror 4 is what is commonly known as a cold filter and is constructed from a coating 4a applied on a transparent substrate 4b such as a glass plate. This coating 4a reflects light of wave-lengths ranging from red color to infrared, while the shorter wavelengths are transmitted therethrough, so that a final red to infrared image of the light source 1 is projected by the photographic objective lens 10 on the cornea 11a of the eye to be examined. Such infrared illumination does not irritate the eye for decrease in the size of the pupil after the eye is accustomed to a dark room. The transmitted light through the mirror 4 is shielded by suitable light absorbing means not shown.

Light reflected from the fundus 11b of the eye 11 passes through the pupil of the eye 11 to the objective lens 10 by which an intermediate image of the fundus 11b is formed between the objective lens 10 and the aperture 9a. This image forming light beam after having passed through the aperture 9a is focused on a light sensitive recording material 13 by an image forming lens 12. To transmit an image forming light beam after the lens 12 away from the recording material 13 to an additional optical system for observation and/or examination of the ocular fundus 11b, there is provided a tiltable mirror 14 positioned at a center between the lens 12 and the recording material 13 to make an angle of 45° with the optical axis of the lens 12. This mirror 14 may be replaced by a cold filter having reflection and transmission characteristics similar to those of the one 4, so that it can be fixedly secured to the housing 37.

The examination optical system comprises a field lens 16 positioned to be rearwardly shifted by a small distance from an ideal focal plane conjugate to the plane of the recording material 13 with respect to the mirror 14, a collimating lens 17 optically aligned to the field lens 16, and a total reflection surface or mirror 18 inclined at an angle of 45° with respect to the common optical axis of the lenses 16 and 17 to reflect an image forming light beam of parallel rays to a collector lens 19 which is positioned in front of an image receiving surface 20a of an infrared image pick-up tube 20. This tube 20 constitutes part of a television camera 21 for producing information of the ocular fundus in the form of electrical signals which are transmitted through a channel 22 to a monitor 23 having a screen 24 on which a visible image of the ocular fundus 11b is formed. While viewing this image, the operator can perform a necessary focusing procedure.

After the condition of best focus is realized, the ocular fundus image of acute rays will be recorded on the material 13 by operating a shutter not shown; for the illuminating optical system, a flash tube 25 is energized as a second light source for production of that acute ray of visible spectrum. The flash tube 25 is associated with a reflector 26 and a condenser lens 27, the second illuminating optical arrangement of these parts 25, 26 and 27 having an optical axis coincident with that of the lenses 5, 7 and 8 and intersect that of the first illuminating optical arrangement of the parts 1, 2 and 3.

The range finding device of the invention includes a pair of objective lenses 33 and 34 fixedly mounted on the housing 37 in an almost common plane to each other and to the photographic objective lens 10 on opposite sides of the optical axis of the lens 10 and oriented so as to form images of slits 32 and 35 behind the lenses 33 and 34 respectively at a common point coincident with that of the intersection of the optical axes of the lenses 33 and 34. The first slit 32 is illuminated by an energized infrared source 31 positioned behind the slit 32. Immediately behind the second slit 35, there is provided a photo-electric transducer 36. During the range scanning process of the camera, the housing 37 is reciprocally moved through an excursion path which is parallel and in axial alignment with the optical axis of the eye 11 to be examined. Suppose the photographic objective lens 10 is at a suitable working distance from the cornea 11a, a sharp image of the first slit 32 is focused by the first objective lens 33 on the iris or sclera of the eye 11 at a point beyond the outer diameter of the annular illuminated zone thereon. Light from the image on the iris or sclera is radiated in all directions by scattering reflection, and a fraction of the light is collected by the second objective lens 34 to form a further image of the first slit 32 on the light sensitive surface of the photo-electric transducer 36 after passing through the opening of the second slit 35.

Since the previously adjusted relative position of the camera is not suited for the working distance, the proportion of that part of the image of the first slit 32 which overlaps the opening of the second slit 35 is decreased with decrease in the intensity of light incident upon the photo-electric transducer 36. As shown in FIG. 2, the output of the photo-electric transducer 36 is amplified by an amplifier circuit 38, and the output of the amplifier circuit 38 is applied to a peak voltage detecting circuit 39 of known construction described as in "Handbook of Practical Electronic Circuits", pp. 459 and 460, (CQ publishing company). When a peak value representative of an optimum working distance is detected by the circuit 39, a switching circuit 40 is actuated, causing an indicator 41 to operate. This indicator 41 produces either a visible or an audible signal only when the optimum working distance and alignment are created between the photographic objective lens 10 and the eye 11. If it is required to indicate the direction in which an adjustment must be made to attain the creation of the working distance, a galvanometer, for example, may be used as arranged to cooperate with the output of the amplifying circuit 38.

The optical aspect of the range finding device of the invention, though have been described as being directed to providing a peak value in variation of the output of the photo-electric transducer 36, may be modified to provide a minimum value when the optimum working distance is established. Many more modifications can be made. For example, instead of using a converging projection light beam, it is possible to use a projection light beam of parallel rays. In this case, if the diameter of the beam from the infrared source 31 is sufficiently small, the first slit 32 and the first objective lens 33 may be omitted. Further the second slit 35 is not always necessary. If so, the light sensitive surface of the photo-electric transducer 36 is in coincidence with the plane which was occupied by the slit 35. It is to be noted here that the construction and arrangement of the various parts of the device shown in FIG. 1 enable the operator to achieve most accurate adjustment of the position of the camera relative to the eye to be examined, provided that the angle between the optical axes of the first and second objective lenses 33 and 34 at the point of intersection thereof is sufficiently large.

While the above-mentioned embodiment of the invention is adapted to correct for the working distance with the help of light rays transmitted from the target on the iris or sclera of the eye by scattering reflection to the photo-electric transducer which functions to sense change in the intensity of light indicent thereon at a fixed area, the present invention provides another example of the range finding device as shown in FIGS. 3A and 3B in which regular reflection of the projected light from the cornea is utilized in combination with a position detector to allow the correction of axial alignment of the camera with the eye to be achieved along with the working distance. In FIG. 3A, an infrared source 31, a slit 32 as a pin-hole and an objective lens or projection lens 33 comprise a projection system for producing a light beam of parallel rays to each other and to the optical axis of the lens 33 with the diameter adjusted to a small value. This light beam is projected to a target area on the cornea of an eye to be examined, and is transmitted by regular reflection back from the target area in a diverging manner to a collector lens 34. A one-dimensional position detector 42, as solid state sensing device, is positioned behind the collector lens 34 with a line in which n number of light sensitive segments S1 to Sn are contiguous to each other disposed in a direction indicated by, d, normal to the optical axis of the collector lens 34 and in a plane containing the optical axes of the lens 33 and 34. The optical axes of the lens 33 and 34 intersect at a point on the optical axis of the photographic objective lens 10. The position of this point is adjusted to coincide with the center of the cornea when the cornea is disposed at an optimum working distance from the photographic objective 10 in axial alignment with each other. Further, the angles of the optical axes of the lenses 33 and 34 with the optical axis of the photographic objective 10 are made equal to each other to allow the collector lens 34 to focus the light at that one of the segments, for example, Sk, which is weighted in light responsibility at a highest rate among the others only when the optical axis of the photographic objective 10 is aligned with the optical axis of the eye 11 to be examined, so that the device of the invention provides an indication of that condition.

Figure 4:
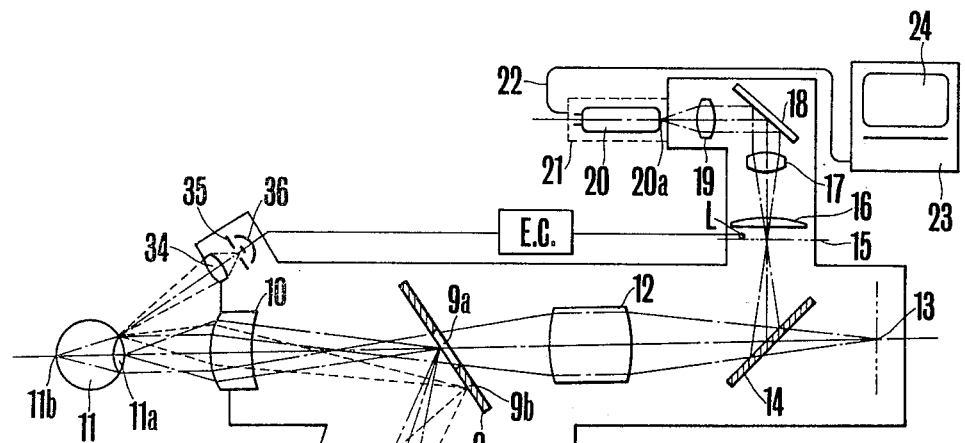
FIG. 4 is a schematic view of still another embodiment of the invention.
Figure 5:
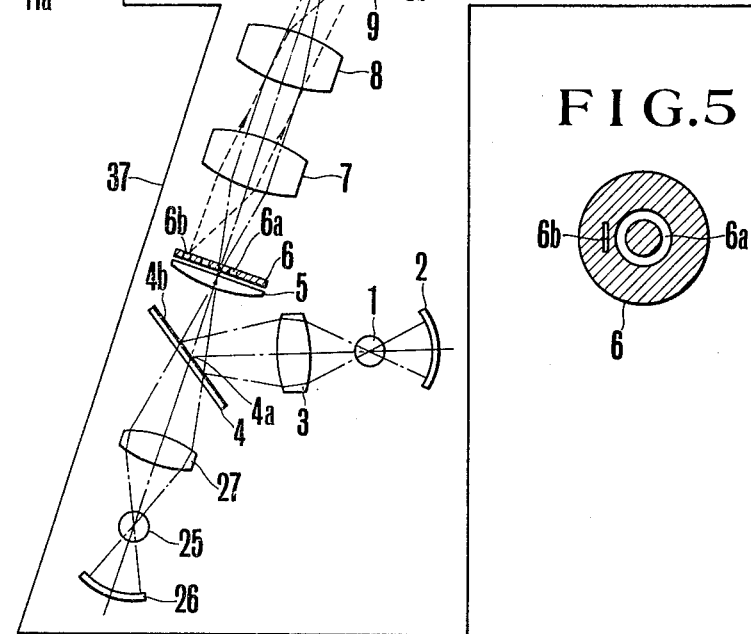
FIG. 5 is a plan view of a diaphragm of FIG. 4 having a ring-shaped aperture with an additional aperture of linear shape for extraction of a range finding beam of infrared light.

FIG. 4 shows an ophthalmoscopic camera of the type which is similar in construction to that of FIG. 1 with a range finding device adapted to make use of an infrared light beam in correcting for the working distance. A projection infrared light beam is emitted from the first illuminating arrangement 1 to 4b by employing a diaphragm of FIG. 5 in place of the diaphragm 6 of FIG. 1. This diaphragm 6 is provided with a slit 6b of a similar shape to that of the slit 32 of FIG. 1 at a location near the outer diameter of the ring-shaped aperture 6a so that when the first light source or incandescent lamp 1 is lit, an infrared light beam from the slit 6b is directed through the relay lenses 7 and 8 to the illuminating mirror 9 and therefrom reflected at a point 9b to the photographic objective 10 by which an image of the slit 6b is formed on the iris or sclera of an eye to be examined at a point corresponding to that of the device of FIG. 1. Light from this image is radiated back in all directions, and a fraction of the light is collected by the lens 34, reaching the light sensitive surface of a photoelectric transducer 36. The output of the transducer 36 is processed by an electrical circuit E.C. to control operation of an indicator or light-emitting diode L as arranged to be viewed near the margin of the field of the sight on the screen 24. The use of infrared light in scanning over the front part of the eye 11a will largely reduce the unpleasant impression of the patient. Another advantage deriving from the fact that the iris of the human eye has a higher reflectance in the infrared region of the electromagnetic spectrum is that the efficiency of the range finding device is improved.

In order to insure the efficiency of the range finding device in the neighborhood or environment of the illuminating light, a visible light may be used as the range scanning light. For this purpose, it is preferred to modify the illuminating mirror 9 in a manner to have a slit at a location 9b instead of in the diaphragm 6. Immediately behind the slit is positioned an incandescent lamp. To afford further discrimination against spurious light in any of the above-mentioned embodiments, there is one technique for imparting to the range scanning light such a discrete property as a flickering of the light source at a predetermined frequency, while the light receiving system is provided with a known filtering means capable of passing a light having the same frequency.

What is claimed is:

1. An eye examining instrument with photo-detecting system comprising:

an eye inspecting system for inspecting an eye including optical objective means opposite to an eye to be examined;

projection means for projecting a beam from an indicium to the eye to be examined; and a photo-detecting system for receiving a beam reflected from the eye, said system having a mask with an area of similar shape as said indicium and a photo-electric transducing means arranged behind the mask, the optical axis of said photo-detecting system crossing the optical axis of said projecting means at a predetermined distance from said eye inspecting system, said photo-electric transducing means producing an electrical signal equal to a predetermined signal when the distance between the eye and said eye examining instrument is proper, and producing a different electrical signal when the distance is erroneous.

2. An eye examining instrument according to claim 1, wherein said projection means optical means for forming an image of the indicium on the eye to be examined at a predetermined position, and said photo-detecting system includes convergent means for focusing the beam from the eye to be examined substantially onto a light receiving surface.

3. An eye examining instrument according to claim 1, wherein said projection means has a luminous indicium and a collimating lens.

4. An eye examining instrument according to claim 1, wherein said inspecting system includes a photographic system for photographing the fundus of the eye to be examined, image transmitting system for transmitting an image of the fundus of the eye to be examined, observation means for observing the image of the fundus of the eye to be examined and illuminating system for illuminating the fundus of the eye to be examined, and further including a housing in which said photographic system, said image transmitting system, and said illuminating system are accommodated, whereby said photo-detecting means are held in said housing.

5. An eye examining instrument according to claim 4, wherein said illuminating system includes a plate provided with a small aperture acting as an indicium.

6. An eye examining instrument according to claim 1, wherein said inspecting system includes a photographic system for photographing the fundus of the eye to be examined, image transmitting system for transmitting an image of the fundus of the eye to be examined, image pick-up means for taking the image of the fundus of the eye to be examined, image display means connected with said image pick-up means to display the image of the fundus of the eye to be examined and illuminating system for illuminating the fundus of the eye to be examined, and further including a housing in which said photographic system, said image transmitting system, said image pick-up means and said illuminating system are accommodated, whereby said projection means and said photo-detecting system are held in said housing.

7. An eye examining instrument according to claim 1 or claim 8, wherein the beam projected by said projection means is an infrared light.

8. An eye examining instrument with a photo-detecting system comprising:

an eye inspecting system for inspecting an eye, including an optical objective means opposite to the eye to be examined;

projection means for projecting a beam from an indicium to the eye to be examined; and a photo-detecting system for receiving a beam reflected by the eye, said system having a position detector having many light receiving regions arranged in the longitudinal direction, the optical axis of said photo-detecting system crossing the optical axis of said projecting means at a predetermined distance from said inspecting system, said position detector producing an electrical signal equal to a predetermined electrical signal when the distance between said eye and said eye examining instrument is proper and producing a different electrical signal when the distance is erroneous.

* * * * *